United States Patent [19]

Bugaut et al.

[11] 4,370,142
[45] Jan. 25, 1983

[54] HAIR-DYEING COMPOSITIONS BASED ON PARA-PHENYLENEDIAMINE AND ORTHO-AMINOPHENOL

[75] Inventors: Andreè Bugaut, Boulogne-Billancourt; Philippe Thouvenin, Aulnay-sous-Bois; Jean Cotteret, Franconville, all of France

[73] Assignee: L'Oreal, Paris, France

[21] Appl. No.: 167,149

[22] Filed: Jul. 8, 1980

[30] Foreign Application Priority Data

Jul. 10, 1979 [FR] France ............................... 79 17889

[51] Int. Cl.³ ................................................ A61K 7/13
[52] U.S. Cl. .......................................... 8/407; 8/410; 8/412; 8/414; 8/416; 8/421
[58] Field of Search .................. 8/412, 407, 410, 416, 8/421

[56] References Cited

U.S. PATENT DOCUMENTS 3,649,159  3/1972  Cohen et al. ............................ 8/412
4,104,021  8/1978  Lapidus et al. ......................... 8/412
4,268,264  5/1981  Grollier et al. ......................... 8/410

Primary Examiner—Donald B. Moyer
Attorney, Agent, or Firm—Fleit & Jacobson

[57] ABSTRACT

The invention relates to compositions for hair dyeing which contain, as the oxidative dye-stuff, in a cosmetically acceptable medium, para-phenylenediamine and ortho-aminophenol, or their cosmetically acceptable salts, in a ratio para-phenylenediamine/ortho-aminophenol which is such that, after the addition of an equal volume of hydrogen peroxide of 20 volumes strength and application to the hair for 30 minutes, no Bandrowsky's base can be detected in the oxidizing dyeing composition.

The compositions according to the invention make it possible to impart background colorations to the hair without the formation of Bandrowsky's base.

12 Claims, No Drawings

HAIR-DYEING COMPOSITIONS BASED ON PARA-PHENYLENEDIAMINE AND ORTHO-AMINOPHENOL

DESCRIPTION

The present invention relates to compositions intended to be used in the so-called oxidation dyeing of the hair, and to the dyeing processes using these compositions.

The use of para-phenylenediamine in hair dyeing, as a so-called oxidation dyestuff precursor of the para-type, is well known. In an oxidizing alkaline medium, and preferably in an ammoniacal medium in the presence of hydrogen peroxide, para-phenylenediamine by itself imparts so-called "background" colorations to the hair, which colorations can range from more or less light chestnuts to very deep browns shaded with red, depending on the concentrations used. In fact, after penetration into the hair fibre, para-phenylenediamine leads, in situ, by means of an oxidative condensation process, to the formation of Bandrowsky's base, which is the coloured product responsible for these so-called "background" colorations. By associating, with para-phenylenediamine in the dyeing compositions for keratin fibres, various compounds commonly referred to as "meta compounds" or "couplers", it is possible to modify these background colorations in order to obtain a whole range of natural shades: black, more or less ashen, more or less warm and rich in very diverse sheens, such as blue, violet or coppery sheens.

The main couplers in current use are phenols, meta-aminophenols, meta-diamines of compounds with an active methylene group. By oxidative coupling with para-phenylenediamine, they lead to the formation of variously coloured indoanilines or indamines.

It is well known that the formation of these coloured compounds competes with the formation of Bandrowsky's base resulting from the oxidative condensation of para-phenylenediamine with itself, which condensation is much slower than that of para-phenylenediamine with the majority of couplers.

It is known, for example, that if para-phenylenediamine is associated either with resorcinol, or with 2,4-diaminoanisole or also meta-aminophenol, in equimolar amounts, the formation of Bandrowsky's base is virtually completely inhibited.

The complete harmlessness of Bandrowsky's base has been questioned in recent years and attempts have therefore been made to suppress its formation on the hair. Thus, in Belgian Pat. No. 597,393, it is specified that, in order to prevent the formation of Bandrowsky's bases, which irritate the skin, products of the 1,4-diaminobenzene type are associated with equimolecular amounts of meta-diaminobenzene, meta-amino-phenol or meta-diphenol. However, we have found that if the couplers are added in a sufficient amount to totally inhibit the formation of Bandrowsky's base, the advantage of the background coloration provided by para-phenylenediamine by itself is largely lost.

Furthermore, it should be noted that certain couplers, in particular the meta-phenylenediamines, such as 2,4-diaminotoluene, are also not completely harmless.

It has already been recommended, in oxidation hair dyeing, to use oxidation dyestuff precursors of the ortho type, in particular ortho-aminophenol. For example, it is known that ortho-aminophenol makes it possible to obtain yellow colorations by oxidation and formation of 2-amino-3H-phenoxazin-3-one. Ortho-aminophenol has also been proposed for use in dyeing compositions containing other oxidation dyestuff precursors, such as oxidation dyestuff precursors of the para type and also meta derivatives or couplers.

We have now discovered, surprisingly, according to the invention, that it is possible to obtain natural shades, possessing a background, which shades are very similar to those imparted to the hair by Bandrowsky's base, albeit more golden and less shaded with red, without the formation of Bandrowsky's base in a chromatographically detectable amount in the oxidising dyeing medium after application on the head for 30 minutes, solely by associating para-phenylene-diamine with or-tho-aminophenol or a cosmetically acceptable salt of these two types of oxidation dyestuff precursors. This result is achieved, depending on the shades which it is desired to obtain, by using para-phenylenediamine and ortho-aminophenol in certain particular molar ratios.

We have also discovered that the background colorations imparted to the hair by the specified combination according to the invention have excellent stability to light, adverse weather conditions and even harsh washing.

This background coloration is essentially due to the formation, using the particular mole ratios and by means of oxidative condensation of the para-phenylenediamine and the ortho-aminophenol, of a new chemical compound containing three nuclei, namely 2-amino-5-para-aminoanilino-N-(para-aminophenyl)-1,4-benzoquinoneimine. In fact, we have found that the rate of formation of this compound, under the conditions of the invention, is much greater than the rate of oxidative condensation of para-phenylenediamine with itself or of orth-aminophenol with itself. Thus this compound is formed at the expense of Bandrowsky's base.

It should furthermore be noted that, compared with Bandrowsky's base, this compound exhibits the advantage of being very harmless.

The present invention thus provides dyeing compositions containing para-phenylenediamine and ortho-aminophenol in well-defined ratios as well as processes for dyeing human hair using para-phenylene-diamine and ortho-aminophenol.

The hair-dyeing composition according to the present invention is essentially characterised in that it contains, as oxidation dyestuffs, in a preferably aqueous, cosmetically acceptable medium permitting the application of the dyestuffs to the hair, para-phenylenediamine, or a cosmetically acceptable salt thereof, and ortho-aminophenol, or a cosmetically acceptable salt thereof, in a molar ratio para-phenylenediamine/ortho-amino-phenol, expressed in terms of free base, which is such that, after the addition of an equal volume of hydrogen peroxide of 20 volumes strength and application to the hair for 30 minutes, no Bandrowsky's base is detected in the oxidising dyeing composition.

It is considered, according to the invention, that no Bandrowsky's base in the oxidizing dyeing composition can be detected when it is not detected by chromatography on a Schleicher and Schüll 1500 LS 254 plate, regardless of the type of carrier used. For this purpose, a spot of a solution of ortho-aminophenol is applied to the plate beforehand, at the point where the oxidising dyeing solution is subsequently to be applied. It is thus possible to have an exact picture of the amount of Bandrowsky's base which has actually been formed during the application of the oxidising dyeing solution to the hair. This is because the ortho-aminophenol prevents the formation of Bandrowsky's base on the silica plate, by the oxidative self-condensation of any para-phenylenediamine which is still present at the end of the application. Para-phenylenediamine has been found to react much more quickly with ortho-aminophenol than with itself.

The dyeing compositions according to the present invention which are more particularly preferred can be classed in two categories according to whether they make it possible to obtain blacks or dark browns, on the one hand, or medium or light chestnuts and blonds, on the other.

The present invention thus provides, on the one hand, hair-dyeing compositions which make it possible to obtain dark shades and which are characterised in that they contain, say, 2.5 to 1% of para-phenylenediamine and in that the molar ratio para-phenylenediamine/ortho-aminophenol is less than or equal to 2, and, on the other hand, dyeing compositions for human hair which lead to medium-light shades or to light and very light shades and which are characterised in that they contain less than 1% of para-phenylenediamine and in that the molar ratio para-phenylenediamine/ortho-aminophenol is less than or equal to 3.

The concentration of para-phenylenediamine in the compositions according to the invention is preferably 0.2 to 2.5% by weight, expressed in terms of free base, and the concentration of ortho-aminophenol is preferably 0.07 to 2.5% by weight of free base and is especially less than 1.75% by weight.

The compositions which are more particularly preferred according to the invention are, in the case of dyeing compositions leading to black and dark brown shades, compositions which contain 1 to 2.5% by weight of para-phenylenediamine and in which the ratio para-phenylenediamine/ortho-aminophenol is greater than or equal to 1 and less than or equal to 2 and preferably greater than or equal to 1.5 and less than or equal to 2, and, in the case of dyeing compositions imparting medium, light and very light shades to the hair, compositions which contain 0.2 to 1% by weight of para-phenylenediamine and in which the ratio para-phenylenediamine/ortho-aminophenol is greater than or equal to 1 and less than or equal to 3 and preferably greater than or equal to 2 and less than or equal to 3.

The cosmetically acceptable salts are preferably hydrochlorides, hydrobromides or sulphates.

As indicated above, the composition according to the invention makes it possible to obtain natural shades without the formation of Bandrowsky's base; it also makes it possible to avoid the use of couplers, such as phenols, meta-diphenols, meta-aminophenols and meta-diamines.

In order to shade and enrich, with a sheen, the colorations obtained using the compositions according to the invention, by adding warm golden or coppery sheens thereto, it is possible to add, to the compositions, direct dyestuffs, such as azo and anthraquinone dyestuffs, and preferably nitrobenzene derivatives, such as 2-amino-3-nitroisopropylbenzene, 2-methyl-4-amino-5-nitrophenol, 2-nitro-4-methyl-6-aminophenol, 3-nitro-6-N-($\beta$-hydroxyethyl)-aminoanisole, 2-amino-3-nitrophenol, 3-N-methylamino-4-nitrophenoxy-ethanol, 2-N-($\beta$-hydroxyethyl)-amino-5-nitrophenoxy-ethanol, 3-nitro-4-N'-($\beta$-hydroxyethyl)-amino-N,N-di-($\beta$-hydroxyethyl)-aniline, 3-nitro-4-N'-methylamino-N-methyl-N-($\beta$-hydroxyethyl)-aniline, 2-N-($\beta$-hydroxyethyl)-amino-5-nitroanisole, 3-nitro-4-aminophenol, 3-nitro-4-N-($\beta$-hydroxyethyl)-aminophenol, ortho-nitroaniline, 3-nitro-4-N'-methylamino-N,N-di-($\beta$-hydroxyethyl)-aniline and also other dyestuffs, such as lawsone.

The colouring agents other than the para-phenylenediamine and the ortho-aminophenol are typically present in an amount from 0.02 to 3% by weight, and preferably 0.1 to 2% by weight, based on the total weight of the composition.

The pH of the dyeing compositions according to the invention is suitably 8 to 11.5 and preferably 9 to 10. The pH of these compositions can be adjusted to the desired value by means of an alkalising agent, such as ammonia, sodium carbonate, potassium carbonate or ammonium carbonate, sodium hydroxide or potassium hydroxide, alkanolamines, such as mono-, di- or triethanolamine, or alkylamines, such as ethylamine or triethylamine.

The dyeing compositions according to the invention can also contain anionic, cationic, non-ionic and/or amphoteric water-soluble surface-active agents. Amongst the surface-active agents which are more particularly preferred, there may be mentioned alkylbenzenesulphonates, alkylnaphthalenesulphonates, sulphates, ether-sulphates and sulphonates of fatty alcohols, quaternary ammonium salts, such as trimethylcetylammonium bromide and cetylpyridinium bromide, diethanolamides of fatty acids, polyoxyethyleneated and polyglycerolated acids and alcohols, polyoxyethyleneated and polyglycerolated alkylphenols and also polyoxyethyleneated alkyl-sulphates. The surface-active products are suitably present in the compositions according to the invention in amounts of 0.5 to 55% by weight, and preferably 4 to 40% by weight, relative to the total weight of the composition.

The compositions can also contain organic solvents for solubilising compounds which would otherwise not be sufficiently soluble in water. Typical such solvents include lower alkanols, such as ethanol and isopropanol, glycerol, glycols or glycol ethers, such as butylglycol, ethylene glycol, propylene glycol, diethylene glycol monoethyl ether and monomethyl ether, and analogous products and mixtures thereof. These solvents are preferably present in proportions from 1 to 40% by weight, and more particularly from 5 to 30% by weight, relative to the total weight of the composition.

The compositions according to the invention can be thickened, preferably with compounds such as sodium aliginate, gum arabic, cellulose derivatives, such as methylcellulose, hydroxy-ethylcellulose, hydroxypropylmethylcellulose and carboxymethylcellulose, and various polymers performing this function, in particular acrylic acid derivatives. It is also possible to use inorganic thickeners, such as bentonite. These thickeners are preferably present in proportions of 0.5 to 5% by weight, and in particular 0.5 to 3% by weight, relative to the total weight of the composition.

Antioxidants, such as sodium sulphite, thioglycolic acid, sodium bisulphite, ascorbic acid and hydroquinone, can also be added to the compositions according to the invention. These antioxidants are advantageously present in the composition in proportions of 0.05 to 1.5% by weight, relative to the total weight of the composition.

It is of course possible to add, to the compositions according to the invention, any other adjuvants normally used in hair-dyeing compositions, in particular penetrating agents, sequestering agents, film-forming agents, buffers and perfumes.

The dyeing compositions according to the invention can be presented in various forms, such as a liquid, cream or gel, or in any other form suitable for dyeing the hair. In particular, they can be packaged in aerosol flasks in the presence of a propellant.

One of the dyeing processes using the dyeing compositions according to the invention consists in mixing the dyeing composition, at the time of use, with a sufficient amount of an oxidising agent, generally as a solution to develop the expected colour, and then in applying the resulting mixture to the hair.

The oxidising solution contains oxidising agents, such as hydrogen peroxide or urea peroxide. Hydrogen peroxide solution of 20 volumes strength is preferably used. The mixture thus obtained is applied to the hair and left for, say, 10 to 30 minutes, after which the hair is rinsed, optionally shampooed and rinsed again, and dried.

The hair-dyeing process using para-phenylenediamine and ortho-aminophenol, according to the invention, for the purpose of inhibiting the formation of Bandrowsky's base on the hair, in the presence of hydrogen peroxide, can also be a two-stage one process.

Initially, a hair composition, typically a lotion containing, say, 2% by weight of ortho-amino-phenol is applied to the hair, and then, after an interval of, say, 10 minutes to allow thorough impregnation of the hair, this optionally being followed by moderate rinsing, a dyeing composition containing para-phenylenediamine and, if appropriate, a direct dyestuff of the type mentioned above is applied, in the presence of hydrogen peroxide. The amounts of lotion containing ortho-aminophenol and of composition containing para-phenylenediamine applied to the head of hair are preferably approximately similar. The concentration of para-phenylenediamine is suitably 0.2 to 2% by weight (free base).

After the pre-lotion containing the ortho-aminophenol has been applied to the hair for about 10 minutes, the hair is only padded in a towel, without rinsing, if the dyeing compositions to be applied in the second stage, in the presence of an equal volume of hydrogen peroxide, lead to black shades or to very dark browns, that is to say if they generally contain 2% to 1% by weight of para-phenylenediamine.

If the dyeing compositions lead to shades ranging from light chestnuts to deep chestnuts and to browns, that is to say if they generally contain from 0.5 to 1% by weight of para-phenylenediamine, the pre-lotion can be followed by moderate rinsing, generally not exceeding 50 ml per gram of hair.

With dyeing compositions leading to light shades, that is to say those generally containing from 0.2 to 0.5% by weight of para-phenylenediamine, rinsing after the pre-lotion can be carried out with up to, say, 75 ml of water per gram of hair.

In the words, after the pre-lotion and optional rinsing, enough ortho-aminophenol to inhibit the formation of Bandrowsky's base must remain on the hair. This amount must be sufficient for the molar ratio para-phenylenediamine/ortho-aminophenol to be within the limits indicated above, depending on the shades which it is desired to obtain on the hair.

It is self-evident that the dyeing compositions used in this two-stage process can contain the adjuvants mentioned above for the composition which can be applied in a single stage.

The following Examples further illustrate the present invention.

EXAMPLE 1

The following dyeing composition is prepared:

| | |
|---|---|
| Para-phenylenediamine | 2 g |
| Ortho-aminophenol | 1 g |
| 3-Nitro-4-aminophenol | 0.7 g |
| 2-Nitro-4-methyl-6-aminophenol | 1.3 g |
| Oxyethyleneated oleyl alcohol containing 2 mols of ethylene oxide (per mol of alcohol) | 4.5 g |
| Oxyethyleneated oleyl alcohol containing 4 mols of ethylene oxide | 4.5 g |
| Ethomeen $TO_{12}$ | 4.5 g |
| Diethanolamides of copra fatty acids | 0.9 g |
| Propylene glycol | 4 g |
| Butylglycol | 8 g |
| 96° strength ethanol | 6 g |
| Masquol DTPA | 2 g |
| Thioglycolic acid | 0.5 g |
| 22° B strength ammonia solution | 12 g |
| Water      q.s.p. | 100 g |
| pH 10.4 | |

100 g of hydrogen peroxide of 20 volumes strength are added at the time of use. When applied for 25 minutes at 30° C. to hair which has been bleached white, this mixture imparts to the hair, after rinsing and shampooing, a red-brown coloration with a rich sheen.

Chromatography of the mixture on a Schleicher and Schüll 1500 LS 254 plate after 25 minutes does not make it possible to detect Bandrowsky's base.

EXAMPLE 2

The following dyeing composition is prepared:

| | |
|---|---|
| Para-phenylenediamine | 2.5 g |
| Ortho-aminophenol | 1.25 g |
| Oxyethyleneated oleyl alcohol containing 2 mols of ethylene oxide | 4.5 g |
| Oxyethyleneated oleyl alcohol containing 4 mols of ethylene oxide | 4.5 g |
| Ethomeen $TO_{12}$ | 4.5 g |
| Diethanolamides of copra fatty acids | 9 g |
| Propylene glycol | 4 g |
| Butylglycol | 8 g |
| 96° strength ethanol | 6 g |
| Masquol DTPA | 2 g |
| Hydroquinone | 0.15 g |
| 35° B strength sodium bisulphite solution | 1.3 g |
| 22° B strength ammonia solution | 5.2 g |
| Water      q.s.p. | 100 g |
| pH 9.9 | |

100 g of hydrogen peroxide of 20 volumes strength are added at the time of use. When applied for 30 minutes at 30° C. to hair which has been bleached white, this mixture imparts to the hair, after rinsing and shampooing, a black coloration.

EXAMPLE 3

The following dyeing composition is prepared:

| | |
|---|---|
| Para-phenylenediamine | 0.8 g |
| Ortho-aminophenol | 0.4 g |
| Carboxymethylcellulose | 2 g |
| Ammonium lauryl-sulphate | 5 g |
| Ammonium acetate | 1 g |
| Propylene glycol | 8 g |
| Masquol DTPA | 2 g |
| Thioglycolic acid | 0.4 g |
| Hydroquinone | 0.15 g |

| -continued | |
|---|---|
| 22° B strength ammonia solution | 3.5 g |
| Water q.s.p. | 100 g |
| pH 9.5 | |

100 g of hydrogen peroxide of 20 volumes strength are added at the time of use. When applied for 20 minutes at 25° C. to hair which has been bleached white, this mixture imparts to the hair, after rinsing and shampooing, a medium chestnut coloration with a golden sheen.

EXAMPLE 4

The following dyeing composition is prepared:

| Para-phneylenediamine | 0.75 g |
|---|---|
| Ortho-aminophenol | 0.375 g |
| Ortho-nitroaniline | 0.2 g |
| 2-Methyl-4-amino-5-nitrophenol | 1.5 g |
| Carboxymethylcellulose | 2 g |
| Ammonium lauryl-sulphate | 5 g |
| Ammonium acetate | 1 g |
| Propylene glycol | 8 g |
| Masquol DTPA | 2 g |
| Thioglycolic acid | 0.4 g |
| Hydroquinone | 0.15 g |
| 22° B strength ammonia solution | 6.5 g |
| Water q.s.p. | 100 g |
| pH 9.8. | |

100 g of hydrogen peroxide of 20 volumes strength are added at the time of use.

When applied to 90% naturally white hair for 30 minutes at 30° C., this mixture imparts a red coloration to the hair.

EXAMPLE 5

The following dyeing composition is prepared:

| Para-phenylenediamine | 0.3 g |
|---|---|
| Ortho-aminophenol | 0.15 g |
| Sodium lauryl-sulphate containing 2 mols of ethylene oxide | 20 g |
| Trilon B | 0.2 g |
| 35° B strength sodium bisulphite solution | 1 g |
| 22° B strength ammonia solution | 10 g |
| Water q.s.p. | 100 g |
| pH 11 | |

100 g of hydrogen peroxide of 20 volume strength are added at the time of use. When applied to 95% naturally white hair for 30 minutes at 30° C., this mixture imparts to the hair, after rinsing and shampooing, a slightly ashen, deep blond coloration.

EXAMPLE 6

The following dyeing composition is prepared:

| Para-phenylenediamine | 0.8 g |
|---|---|
| Ortho-aminophenol | 0.266 g |
| 2-Amino-3-nitrophenol | 0.45 g |
| Oxyethyleneated oleyl alcohol containing 2 mols of ethylene oxide | 4.5 g |
| Oxyethyleneated oleyl alcohol containing 4 mols of ethylene oxide | 4.5 g |
| Ethomeen TO$_{12}$ | 4.5 g |
| Diethanolamides of copra fatty acids | 9 g |
| Propylene glycol | 4 g |
| Butylglycol | 8 g |
| 96° strength ethanol | 6 g |
| Masquol DTPA | 2 g |

| -continued | |
|---|---|
| Hydroquinone | 0.15 g |
| Thioglycolic acid | 0.4 g |
| 22° B strength ammonia solution | 1.2 g |
| Water q.s.p. | 100 g |
| pH 9.1 | |

100 g of hydrogen peroxide of 20 volumes strength are added at the time of use. When applied to 90% naturally white hair for 20 minutes at 25° C., this mixture imparts to the hair, after rinsing and shampooing, a coppery deep chestnut coloration.

EXAMPLE 7

The following dyeing composition is prepared:

| Para-phenylenediamine | 1.2 g |
|---|---|
| Ortho-aminophenol | 0.6 g |
| 3-Nitro-4-(β-hydroxyethyl)-aminophenol | 0.5 g |
| 3-Nitro-4-aminophenol | 0.1 g |
| Oxyethyleneated oleyl alcohol containing 2 mols of ethylene oxide | 4.5 g |
| Oxyethyleneated oleyl alcohol containing 4 mols of ethylene oxide | 4.5 g |
| Ethomeen TO$_{12}$ | 4.5 g |
| Diethanolamides of copra fatty acids | 9 g |
| Propylene glycol | 4 g |
| Butylglycol | 8 g |
| 96° strength ethanol | 6 g |
| Masquol DTPA | 2 g |
| Hydroquinone | 0.15 g |
| Thioglycolic acid | 0.4 g |
| 22° B strength ammonia solution | 10 g |
| Water q.s.p. | 100 g |
| pH 10.5 | |

100 g of hydrogen peroxide of 20 volumes strength are added at the time of use. When applied to 90% naturally white hair for 30 minutes at 27° C., this mixture imparts to the hair, after rinsing and shampooing, a very dark red-brown coloration.

EXAMPLE 8

The following dyeing composition is prepared:

| Para-phenylenediamine | 1 g |
|---|---|
| Ortho-aminophenol | 0.33 g |
| Cemulsol NP$_4$ | 21 g |
| Cemulsol NP$_9$ | 24 g |
| Oleic acid | 4 g |
| Butylglycol | 3 g |
| 96° strength alcohol | 10 g |
| Masquol DTPA | 2.5 g |
| Thioglycolic acid | 0.6 g |
| 22° B strength ammonia solution | 10 g |
| Water q.s.p. | 100 g |
| pH 10.3 | |

100 g of hydrogen peroxide of 20 volumes strength are added at the time of use.

When applied for 30 minutes at 27° C. to hair which has been bleached white, this mixture imparts to the hair, after rinsing and shampooing, a golden medium chestnut coloration.

EXAMPLE 9

The following dyeing composition is prepared:

| Para-phenylenediamine | 2.5 g |
|---|---|
| Ortho-aminophenol | 1.25 g |
| Cemulsol NP$_4$ | 21 g |

| | |
|---|---|
| Cemulsol NP₉ | 24 g |
| Oleic acid | 4 g |
| Butylglycol | 3 g |
| 96° strength alcohol | 10 g |
| Masquol DTPA | 2.5 g |
| Thioglycolic acid | 0.6 g |
| 22° B strength ammonia solution | 10 g |
| Water q.s.p. | 100 g |
| pH 10.3 | |

100 g of hydrogen peroxide of 20 volumes strength are added at the time of use. When applied for 30 minutes at 25° C. to hair which has been bleached white, this mixture imparts to the hair, after rinsing and shampooing, a black coloration with a violet sheen.

EXAMPLE 10

The following dyeing composition is prepared:

| | |
|---|---|
| Para-phenylenediamine | 0.9 g |
| Ortho-aminophenol | 0.36 g |
| 3-Nitro-4-methylamino-N,N-di-($\beta$-hydroxyethyl)-aniline | 0.7 g |
| Cemulsol NP₄ | 21 g |
| Cemulsol NP₉ | 24 g |
| Oleic acid | 4 g |
| Butylglycol | 3 g |
| 96° strength alcohol | 10 g |
| Masquol DTPA | 2.5 g |
| Thioglycolic acid | 0.6 g |
| 22° B strength ammonia solution | 10 g |
| Water q.s.p. | 100 g |
| pH 10.3 | |

100 g of hydrogen peroxide of 20 volumes strength are added at the time of use. When applied for 25 minutes at 30° C. to hair which has been bleached white, this mixture imparts to the hair, after rinsing and shampooing, a medium chestnut coloration.

EXAMPLE 11

The following dyeing composition is prepared:

| | |
|---|---|
| Para-phenylenediamine | 1.5 g |
| Ortho-aminophenol | 0.86 g |
| 3-Nitro-4-aminophenol | 0.85 g |
| Oxyethyleneated oleyl alcohol containing 2 mols of ethylene oxide | 4.5 g |
| Oxyethyleneated oleyl alcohol containing 4 mols of ethylene oxide | 4.5 g |
| Ethomeen TO₁₂ | 4.5 g |
| Diethanolamides of copra fatty acids | 9 g |
| Propylene glycol | 4 g |
| Butylglycol | 8 g |
| 96° strength ethanol | 6 g |
| Masquol DTPA | 2 g |
| Thioglycolic acid | 0.5 g |
| 22° B strength ammonia solution | 4.1 g |
| Water q.s.p. | 100 g |
| pH 9.7 | |

100 g of hydrogen peroxide of 20 volumes strength are added at the time of use. When applied to bleached hair for 30 minutes at 27° C., this mixture imparts to the hair, after rinsing and shampooing, a coppery deep chestnut coloration.

EXAMPLE 12

The following dyeing composition is prepared:

| | |
|---|---|
| Para-phenylenediamine | 0.3 g |
| Ortho-aminophenol | 0.1 g |
| Lawsone | 0.5 g |
| Oxyethyleneated oleyl alcohol containing 2 mols of ethylene oxide | 4.5 g |
| Oxyethyleneated oleyl alcohol containing 4 mols of ethylene oxide | 4.5 g |
| Ethomeen TO₁₂ | 4.5 g |
| Diethanolamides of copra fatty acids | 9 g |
| Propylene glycol | 4 g |
| Butylglycol | 8 g |
| 96° strength ethanol | 6 g |
| Masquol DTPA | 2 g |
| Thioglycolic acid | 0.5 g |
| Triethanolamine | 3 g |
| Water q.s.p. | 100 g |
| pH 8.5 | |

100 g of hydrogen peroxide of 20 volumes strength are added at the time of use. When applied for 25 minutes at 30° C. to hair which has been bleached white, this mixture imparts to the hair, after rinsing and shampooing, a golden blond coloration.

EXAMPLE 13

The following dyeing composition is prepared:

| | |
|---|---|
| Para-phenylenediamine | 1.5 g |
| Ortho-aminophenol | 0.75 g |
| Remcopal 334 | 21 g |
| Remcopal 349 | 24 g |
| Oleic acid | 4 g |
| Butylglycol | 3 g |
| 96° strength ethanol | 10 g |
| Masquol DTPA | 2.5 g |
| 35° B strength sodium bisulphite solution | 1 g |
| 22° B strength ammonia solution | 10 g |
| Water q.s.p. | 100 g |
| pH 10.6 | |

100 g of hydrogen peroxide of 20 volumes strength are added at the time of use.

When applied to 90% naturally white hair for 20 minutes at 25° C., this mixture imparts to the hair, after rinsing and shampooing, a very dark brown coloration.

EXAMPLE 14

The following dyeing composition is prepared:

| | |
|---|---|
| Para-phenylenediamine | 0.5 g |
| Ortho-aminophenol | 0.166 g |
| Carbopol 934 | 1.5 g |
| 96° strength ethanol | 11 g |
| Butylglycol | 5 g |
| Trimethylcetylammonium bromide | 1 g |
| Trilon B | 0.1 g |
| 22° B strength ammonia solution | 10 g |
| Thioglycolic acid | 0.2 g |
| Water q.s.p. | 100 g |
| pH 10.4 | |

100 g of hydrogen peroxide of 20 volumes strength are added at the time of use. When applied for 25 minutes at 30° C. to hair which has been bleached white, this mixture imparts to the hair, after rinsing and shampooing, a golden hazel coloration.

EXAMPLE 15

The following dyeing composition is prepared:

| | |
|---|---|
| Para-phenylenediamine | 0.24 g |
| Ortho-aminophenol | 0.12 g |
| 3-Nitro-4-methylamino-N,N-di-(β-hydroxyethyl)-aniline | 1 g |
| Carbopol 934 | 1.5 g |
| 96° strength ethanol | 11 g |
| Butylglycol | 5 g |
| Trimethylcetylammonium bromide | 1 g |
| Trilon B | 0.1 g |
| 22° B strength ammonia solution | 10 g |
| Thioglycolic acid | 0.2 g |
| Water q.s.p. | 100 g |
| pH 10.4 | |

100 g of hydrogen peroxide of 20 volumes strength are added at the time of use. When applied for 20 minutes at 25° C. to hair which has been bleached straw yellow, this mixture imparts to the hair, after rinsing and shampooing, a very dark purple-violet coloration.

EXAMPLE 16

The following dyeing composition is prepared:

| | |
|---|---|
| Para-phenylenediamine | 1 g |
| Ortho-aminophenol | 0.5 g |
| Remcopal 334 | 21 g |
| Remcopal 349 | 24 g |
| Oleic acid | 4 g |
| Butylglycol | 3 g |
| 96° strength ethanol | 10 g |
| Masquol DTPA | 2.5 g |
| 35° B strength sodium bisulphite solution | 1 g |
| 22° B strength ammonia solution | 10 g |
| Water q.s.p. | 100 g |
| pH 10.6 | |

100 g of hydrogen peroxide of 20 volumes strength are added at the time of use. When applied to 90% naturally white hair for 20 minutes at 25° C., this mixture imparts to the hair, after rinsing and shampooing, a medium golden chestnut coloration.

EXAMPLE 17

The following dyeing composition is prepared:

| | |
|---|---|
| Para-phenylenediamine | 1.8 g |
| Ortho-aminophenol | 1.2 g |
| 3-Nitro-4-methylamino-N,N-di-(β-hydroxyethyl)-aniline | 0.4 g |
| Remcopal 334 | 21 g |
| Remcopal 349 | 24 g |
| Oleic acid | 4 g |
| Butylglycol | 3 g |
| 96° strength ethanol | 10 g |
| Masquol DTPA | 2.5 g |
| 35° B strength sodium bisulphite solution | 1 g |
| 22° B strength ammonia solution | 10 g |
| Water q.s.p. | 100 g |
| pH 10.6 | |

100 g of hydrogen peroxide of 20 volumes strength are added at the time of use.

When applied to 90% naturally white hair for 30 minutes at 30° C., this mixture imparts to the hair, after rinsing and shampooing, a raven black coloration.

In the various examples above, chromatography on a Schleicher and Schüll 1500 LS 254 plate did not make it possible to detect the formation of Bandrowsky's Base after 30 minutes.

EXAMPLE 18

(1) The lotion ($a_1$) is prepared in the form of a cream:

| | |
|---|---|
| Ortho-aminophenol | 2 g |
| Alfol $C_{16}/C_{18}$ (50/50) | 14.4 g |
| Lanette wax E $C_{16}/C_{18}$ (50/50) | 3.6 g |
| Cemulsol B | 1.8 g |
| Monoethanolamine q.s.p. | pH 7 |
| Water q.s.p. | 100 g |

(2) The following dyeing composition ($b_1$) is prepared:

| | |
|---|---|
| Para-phenylenediamine | 0.4 g |
| 3-Nitro-4-N-(β-hydroxyethyl)-aminophenol | 0.2 g |
| 2-Amino-3-nitrophenol | 0.1 g |
| Sodium lauryl-sulphate containing 2 mols of ethylene oxide | 20 g |
| Trilon B | 0.2 g |
| 35° B strength sodium bisulphite solution | 1 g |
| 22° B strength ammonia solution | 10 g |
| Water q.s.p. | 100 g |
| pH 10.8 | |

5 g of the pre-lotion ($a_1$) are applied to 4 g of 90% naturally white hair. After an interval of 10 minutes, the hair is rinsed with 300 ml of water. It is padded with a towel and 2.5 g of the dyeing composition ($b_1$) are then applied after an equal weight of hydrogen peroxide of 20 volumes strength has been added thereto. After an interval of 30 minutes at 30° C., rinsing and shampooing, a very luminous, golden chestnut coloration is obtained.

In a sample of oxidising composition taken after an interval of 30 minutes, no Bandrowsky's Base is detected by chromatography on a Schleicher and Schüll F 1500 LS 254 plate, taking the precautions indicated above.

EXAMPLE 19

(1) The lotion ($a_2$) is prepared in the form of a gel:

| | |
|---|---|
| Ortho-aminophenol | 2 g |
| Remcopal 334 | 11 g |
| Remcopal 349 | 11 g |
| Propylene glycol | 5.5 g |
| 96° strength alcohol | 4 g |
| Monoethanolamine q.s.p. | pH 7 |
| Water q.s.p. | 100 g |

(2) The following dyeing composition ($b_2$) is prepared:

| | |
|---|---|
| Para-phenylenediamine | 0.75 g |
| 3-Nitro-4-N'-methylamino-N,N-di-(β-hydroxyethyl)-aniline | 0.36 g |
| Carboxymethylcellulose | 2 g |
| Ammonium lauryl-sulphate | 5 g |
| Ammonium acetate | 1 g |
| Propylene glycol | 8 g |
| Masquol DTPA | 2 g |
| Thioglycolic acid | 0.4 g |
| Butylglycol | 8 g |
| 22° B strength ammonia solution | 3 g |
| Water q.s.p. | 100 g |
| pH 9.5 | |

5 g of the pre-lotion (a₂) are applied to 4 g of 90% naturally white hair. After an interval of 10 minutes, the hair is rinsed with 200 ml of water. It is padded in a towel and 2.5 g of the dyeing composition (b₂) are then applied after an equal weight of hydrogen peroxide of 20 volumes strength has been added thereto. After an interval of 25 minutes at 28° C., rinsing and shampooing, a deep chestnut coloration is obtained.

In a sample of oxidising composition taken after an interval of 25 minutes, no Bandrowsky's Base is detected on a Schleicher and Schüll F 1500 LS 254 plate, taking the precautions indicated above.

EXAMPLE 20

(1) The lotion (a₂) in the form of a gel, described in Example 19, is prepared.

(2) The following dyeing composition (b₃) is prepared:

| | |
|---|---|
| Para-phenylenediamine | 2 g |
| Carbopol 934 | 1.5 g |
| 96° strength ethanol | 11 g |
| Butylglycol | 5 g |
| Trimethylcetylammonium bromide | 1 g |
| Trilon B | 0.1 g |
| 22° B strength ammonia solution | 10 g |
| Thioglycolic acid | 0.2 g |
| Water q.s.p. | 100 g |
| pH 10.3 | |

5 g of the pre-lotion (a₂) are applied to 4 g of hair which has been bleached white. After an interval of 10 minutes, the hair is padded in a towel and 2.5 g of the dyeing composition (b₃) are then applied after an equal weight of hydrogen peroxide of 20 volumes strength has been added thereto. After an interval of 30 minutes at 30° C., rinsing and shampooing, a black-brown coloration is obtained.

In a sample of oxidising composition taken after an interval of 30 minutes, no Bandrowsky's Base is detected by chromatography on a Schleicher and Schüll F 1500 LS 254 plate, taking the precautions indicated above.

EXAMPLE 21

(1) The foaming lotion (a₃) is prepared:

| | |
|---|---|
| Ortho-aminophenol | 2 g |
| Remcopal 334 | 22 g |
| Remcopal 349 | 22 g |
| Propylene glycol | 11 g |
| 96° strength alcohol | 8 g |
| Triethanolamine q.s.p. | pH 7 |
| Water q.s.p. | 100 g |

(2) The dyeing composition (b₄) is prepared:

| | |
|---|---|
| Para-phenylenediamine | 1 g |
| Remcopal 334 | 21 g |
| Remcopal 349 | 24 g |
| Oleic acid | 4 g |
| Butylglycol | 3 g |
| 96° strength ethanol | 10 g |
| Masquol DTPA | 2.5 g |
| 35° B strength sodium bisulphite solution | 1 g |
| 22° B strength ammonia solution | 10 g |
| Water q.s.p. | 100 g |
| pH 10.6 | |

5 g of the pre-lotion (a₃) are applied to 4 g of hair which has been bleached white. After an interval of 10 minutes, the hair is rinsed with 200 ml of water. It is padded with a towel and 2.5 g of the dyeing composition (b₄) are then applied after an equal weight of hydrogen peroxide of 20 volumes strength has been added thereto. After an interval of 30 minutes at 30° C., rinsing and shampooing, a deep chestnut coloration is obtained.

In a sample of oxidising composition taken after an interval of 30 minutes, no Bandrowsky's Base is detected by chromatography on a Schleicher and Schüll F 1500 LS 254 plate, taking the precautions indicated above.

EXAMPLE 22

(1) The lotion (a₁) in the form of a cream, described in Example 18, is prepared.

(2) The following dyeing composition (b₅) is prepared:

| | |
|---|---|
| Para-phenylenediamine | 0.5 g |
| Oxyethyleneated oleyl alcohol containing 2 mols of ethylene oxide | 4.5 g |
| Oxyethyleneated oleyl alcohol containing 4 mols of ethylene oxide | 4.5 g |
| Ethomeen TO₁₂ | 4.5 g |
| Ethanolamides of copra fatty acids | 9 g |
| Propylene glycol | 4 g |
| Butylglycol | 8 g |
| 96° strength ethanol | 6 g |
| Masquol DTPA | 2 g |
| Thioglycolic acid | 0.5 g |
| 22° B strength ammonia solution | 10 g |
| Water q.s.p. | 100 g |
| pH 10.5 | |

5 g of the pre-lotion (a₁) are applied to 4 g of 90% naturally white hair. After an interval of 10 minutes, the hair is rinsed with 300 ml of water. It is padded in a towel and 2.5 g of the dyeing composition (b₅) are then applied after an equal weight of hydrogen peroxide of 20 volumes strength has been added thereto. After an interval of 30 minutes at 30° C., rinsing and shampooing, a very golden, light chestnut coloration is obtained.

In a sample of oxidising composition taken after an interval of 30 minutes, no Bandrowsky's Base is detected on a Schleicher and Schüll F 1500 LS 254 plate, taking the precautions indicated above.

EXAMPLE 23

The following lotion (a₄) is prepared:

| | |
|---|---|
| Ortho-aminophenol | 2 g |
| Oxyethyleneated oleyl alcohol containing 2 mols of ethylene oxide | 4.5 g |
| Oxyethyleneated oleyl alcohol containing 4 mols of ethylene oxide | 4.5 g |
| Ethomeen TO₁₂ | 4.5 g |
| Ethanolamides of copra fatty acids | 9 g |
| Propylene glycol | 4 g |
| Butylglycol | 8 g |
| 96° strength ethanol | 6 g |
| Masquol DTPA | 2 g |
| Thioglycolic acid | 0.5 g |
| Water q.s.p. | 100 g |
| pH 7.5 | |

(2) The following dyeing composition (b₆) is prepared:

| | | |
|---|---|---|
| Para-phenylenediamine | 1.2 g | |
| 3-Nitro-4-aminophenol | 0.5 g | |
| Oxyethyleneated oleyl alcohol containing 2 mols of ethylene oxide | 4.5 g | |
| Oxyethyleneated oleyl alcohol containing 4 mols of ethylene oxide | 4.5 g | |
| Ethomeen TO$_{12}$ | 4.5 g | |
| Ethanolamides of copra fatty acids | 9 g | |
| Propylene glycol | 4 g | |
| Butylglycol | 8 g | |
| 96° strength ethanol | 6 g | |
| Masquol DTPA | 2 g | |
| Thioglycolic acid | 0.5 g | |
| 22° B strength ammonia solution | 10 g | |
| Water q.s.p. | 100 g | |
| pH 10.7 | | |

5 g of the pre-lotion (a$_4$) are applied to 4 g of 90% naturally white hair. After an interval of 10 minutes, the hair is padded in a towel and 2.5 g of the dyeing composition (b$_6$) are then applied after an equal weight of hydrogen peroxide of 20 volumes strength has been added thereto. After an interval of 30 minutes at 30° C., rinsing and shampooing, a brown coloration with a coppery sheen is obtained.

In a sample of the oxidising composition taken after an interval of 30 minutes, no Bandrowsky's Base is detected by chromatography on a Schleicher and Schüll F 1500 LS 254 plate, taking the precautions indicated above.

In the above examples, the trade products are constituted as follows:

Ethomeen TO$_{12}$: oxyethyleneated oleylamine containing 12 mols of ethylene oxide, sold by Armour Hess Chemical Ltd;

Masquol DTPA: the pentasodium salt of diethylenetriaminepentaacetic acid, sold by Protex;

Trilon B: ethylenediaminetetraacetic acid;

Cemulsol NP$_4$: nonylphenol containing 4 mols of ethylene oxide, sold by Rhône-Poulenc;

Cemulsol NP$_9$: nonylphenol containing 9 mols of ethylene oxide, sold by Rhône-Poulenc;

Carbopol 934: crosslinked polyacrylic acid sold by Goodrich Chemicals;

Remcopal 334: oxyethyleneated nonylphenol containing 4 mols of ethylene oxide, sold by Gerland;

Remcopal 349: oxyethyleneated nonylphenol containing 9 mols of ethylene oxide, sold by Gerland;

Alfol C$_{16}$/C$_{18}$ (50/50): cetylstearyl alcohol sold by Condea;

Lanette wax E C$_{16}$/C$_{18}$ (50/50): sulphated cetyl/stearyl alcohol sold by Henkel; and Cemulsol B: oxyethyleneated castor oil sold by Rhône-Poulenc.

EXAMPLE 24

Preparation of 2-amino-5-(p-aminoanilino)-N-(p-aminophenyl)-1,4-benzoquinoneimine.

0.165 mol (17.92 g) of para-phenylenediamine and 0.164 mol (17.92 g) of ortho-aminophenol are dissolved in 800 ml of water to which 240 ml of 22° B strength ammonia solution have been added. 1,040 ml of hydrogen peroxide of 20 volumes strength are added and the reaction medium is stirred for 5 hours at ambient temperature. The mixture is filtered and the expected product which has precipitated is washed with water. After drying, it melts at 200° C.

| Analysis | Calculated for C$_{18}$H$_{17}$N$_5$O | Found |
|---|---|---|
| C % | 67.69 | 67.51 |
| H % | 5.37 | 5.62 |
| N % | 21.93 | 21.69 |

Molecular weight calculated for C$_{18}$H$_{17}$N$_5$O: M=319.
Molecular weight found by mass spectroscopy: M=319.

The following structure was confirmed by a study of the NMR spectrum:

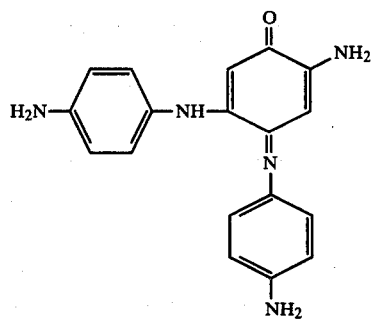

We claim:
1. A composition suitable for dyeing human hair which contains, in a cosmetically acceptable medium, paraphenylenediamine, or a cosmetically acceptable salt thereof, and ortho-aminophenol, or a cosmetically acceptable salt thereof, in a molar ratio para-phenylenediamine/orthoaminophenol which is less than or equal to 2:1 in the case para-phenylenediamine is present in an amount of 1 to 2.5% by weight and which is greater than or equal to 1:1 and less than or equal to 3:1 in the case para-phenylenediamine is present in an amount of 0.2 to 1% by weight.

2. A composition according to claim 1 in which ortho-aminophenol is present in an amount of 0.07 to 2.5% by weight.

3. A composition according to claim 2 in which the molar ratio para-phenylenediamine/ortho-aminophenol is greater than or equal to 1:1 and less than or equal to 2:1.

4. A composition according to claim 1 which additionally contains at least one direct dyestuff.

5. A composition according to claim 4 in which the direct dyestuff is a nitrobenzene derivative.

6. A composition according to claim 1 which has a pH of 8 to 11.5.

7. A composition according to claim 1 in which the cosmetically acceptable medium is aqueous and contains one or more of the following adjuvants: an anionic, cationic, non-ionic or amphoteric water-soluble surface-active agent or a mixture thereof, an organic solvent, thickener, antioxidant, penetrating agent, sequestering agent, film-forming polymer, buffer or perfume.

8. Process for dyeing the hair which comprises mixing a composition as defined in claim 1 with an oxidising agent which is hydrogen peroxide or urea peroxide, and applying the resulting mixture to the hair for 10 to 30 minutes.

9. Process for dyeing the hair, which comprises applying thereto a dyeing composition containing ortho-aminophenol, allowing the composition to impregnate the hair, optionally rinsing the hair and applying a dyeing composition containing paraphenylenediamine with an oxidising agent which is hydrogen peroxide or urea peroxide, the optional rinsing of the hair being carried out so as to leave, on the latter, a sufficient amount of ortho-aminophenol to prevent the formation of Bandrowsky's base during the coloration on the hair.

10. Process according to claim 9, which comprises applying a pre-lotion containing about 2% by weight of ortho-aminophenol and, after towel-drying, applying a composition containing 1 to 2% by weight of paraphenylenediamine in the presence of an equal volume of hydrogen peroxide.

11. Process according to claim 9, which comprises applying a pre-lotion containing about 2% by weight of ortho-aminophenol and, after rinsing with water in an amount not exceeding 50 ml/g of hair, applying a composition containing 0.5 to 1% by weight of paraphenylenediamine.

12. Process according to claim 9, which comprises applying a pre-lotion containing about 2% of ortho-aminophenol, and after rinsing with water in an amount up to 75 ml/g of hair, applying a composition containing 0.2 to 0.5% by weight of paraphenylenediamine.

* * * * *